(12) United States Patent
Contractor et al.

(10) Patent No.: US 6,437,193 B1
(45) Date of Patent: Aug. 20, 2002

(54) VAPOR PHASE OXIDATION OF PROPYLENE TO ACROLEIN

(75) Inventors: Rashmikant Maganlal Contractor, Wilmington, DE (US); Mark William Andersen, Charlottesville, VA (US); Daniel Campos, Wilmington, DE (US); Gerard Hecquet, Bethune (FR); Roland Kotwica, Pontpoint (FR); Charlotte Pham, Saverne (FR); Michel Simon, St. Avold (FR); Mireille Stojanovic, Paris (FR)

(73) Assignees: E. I. du Pont de Nemours and Company, Wilmington, DE (US); Atofina, Paris (FR)

( * ) Notice: Subject to any disclaimer, the term of this patent is extended or adjusted under 35 U.S.C. 154(b) by 0 days.

(21) Appl. No.: 09/543,835

(22) Filed: Apr. 6, 2000

Related U.S. Application Data

(63) Continuation-in-part of application No. 09/113,259, filed on Jul. 10, 1998.
(60) Provisional application No. 60/055,693, filed on Jul. 15, 1997.

(51) Int. Cl.$^7$ .............................................. C07C 45/35
(52) U.S. Cl. ........................ 568/479; 568/470; 568/475; 568/476; 568/480; 502/212
(58) Field of Search ................................ 568/470, 471, 568/477, 479, 480, 476, 475; 502/38, 212

(56) References Cited

U.S. PATENT DOCUMENTS

| | | | |
|---|---|---|---|
| 3,487,109 A | 12/1969 | Kurata et al. | 260/533 |
| 3,631,099 A | 12/1971 | Eden | 260/533 N |
| 3,639,269 A | 2/1972 | Koberstein et al. | 252/437 |
| 3,761,424 A | 9/1973 | Koberstein et al. | 252/437 |
| 3,875,220 A | 4/1975 | White et al. | 260/530 N |
| 4,102,914 A | 7/1978 | Beuther et al. | 260/465.3 |
| 4,152,393 A | 5/1979 | Callahan et al. | 422/144 |
| 4,341,717 A | 7/1982 | Callahan et al. | 260/465.3 |
| 4,442,308 A | 4/1984 | Arntz et al. | 568/480 |
| 4,604,370 A | 8/1986 | Sarumaru et al. | 502/38 |
| 4,621,072 A | 11/1986 | Arntz et al. | 502/504 |
| 4,659,689 A | 4/1987 | Suresh et al. | 23/4 |
| 4,668,802 A | 5/1987 | Contractor | 549/259 |
| 4,677,084 A | 6/1987 | Bergna | 502/8 |
| 4,769,477 A | 9/1988 | Bergna | 549/259 |
| 5,072,052 A | 12/1991 | Boeck et al. | 568/479 |
| 5,082,819 A | 1/1992 | Boeck et al. | 502/212 |
| 5,519,149 A | 5/1996 | Contractor et al. | 307/34 |

FOREIGN PATENT DOCUMENTS

| | | | |
|---|---|---|---|
| DE | 44 36 385 | 10/1994 | C07B/35/04 |
| EP | 0 034 442 | 8/1981 | C07C/45/34 |
| EP | 0861819 A1 | 11/1998 | C07C/45/28 |
| EP | 0861821 A1 | 11/1998 | C07C/51/16 |
| GB | 1307936 | 2/1973 | C07C/47/22 |
| GB | 1490489 | 11/1977 | C07C/47/22 |
| JP | 3-170445 | 7/1991 | C07C/27/12 |
| JP | 05301051 | of 1996 | |

OTHER PUBLICATIONS

Advertising, Chemicals Technologies Worldwide, 1973.
James L. Callahan et al., Oxidation and Ammoxidation Of Propylene Over Bismuth Molybdate Catalyst, *Ind. Eng. Chem. Prod. Res. Develop.*, vol. 9, No. 2, 134–142, 1970.
Robert K. Grasselli et al., Selective Oxidation And Ammoxidation Of Propylene By Heterogeneous Catalysis, *Academic Press, Inc.*, vol. 30, 133–163, 1981.
G. S. Patience et al., Modelling Of Propylene Oxidation In A Circulating Fluidized–Bed Reactor, *Elsevier Science B. V.*, 1–18, 1994.

*Primary Examiner*—Sreeni Padmanabhan

(57) ABSTRACT

An improved method for the selective vapor phase oxidation of propylene to acrolein in a recirculating solids reactor system using a bismuth molybdate multimetal oxide involving specific reactant concentrations (preferably 5 mol % to 30 mol % propylene, 0 to 20 mol % oxygen, and the remainder inert gas), particle size (1 to 300 micrometers), temperature (250 to 450° C.) and gas (1 to 15 seconds) and solids (2 to 60 seconds) residence times. Such a process leads to improved selectivity and propylene conversion.

11 Claims, 1 Drawing Sheet

VAPOR PHASE OXIDATION OF PROPYLENE TO ACROLEIN

CROSS-REFERENCE TO RELATED APPLICATIONS

This is a continuation-in-part of application Ser. No. 09/113,259 filed Jul. 10, 1998, that claims the benefit of priority to provisional application No. 60/055,693 filed Jul. 15, 1997.

STATEMENT REGARDING FEDERALLY SPONSORED RESEARCH OR DEVELOPMENT

"Not Applicable"

BACKGROUND OF THE INVENTION

1. Field of the Invention

This invention relates to an improved vapor phase process for the catalytic oxidation of propylene to acrolein using as oxidant reducible particulate solids in an oxidized state, and where the resulting reduced solids are separately regenerated using molecular oxygen.

2. Description of Related Art

An important route to acrolein is the vapor phase oxidation of propylene over a multicomponent catalyst containing molybdenum and/or other metals, usually as their oxides. The reaction step involves oxidation of propylene with air (oxygen) to form acrolein, along with carbon oxides, water and smaller amounts of other oxidized byproducts. Typically the reaction is carried out in multitubular fixed-bed reactors. The large exothermic heat of reaction and the thermal sensitivity of the propylene oxidation requires low feed concentrations, expensive heat transfer equipment, handling of a large volume of gas, and good reactor temperature control. Low propylene concentration is also required to avoid flammability conditions.

The magnitude of some of these problems is reduced when a fluidized-bed reactor is used. The temperature can be readily controlled within a few degrees because of the intensive solids mixing and the good heat transfer characteristics. Higher propylene concentrations can be used because the danger of flammability is reduced by introducing the propylene directly into the reactor rather than pre-mixing it with air (oxygen). However, very high propylene concentrations and low oxygen-to-propylene ratios in the reactor may result in the over reduction of the solids and reduced selectivity to acrolein. Also, significant back-mixing of gases in the fluidized-bed reactor result in poorer contact between gases in the bubbles and the solids, making it difficult to obtain high propylene conversion.

Modified forms of fluidized-bed reactor are known as recirculating solids reactor, transport bed reactor, transport line reactor, riser reactor, fluidization reactor, multi-chamber fluidized bed reactor, and by other names, depending on design and/or personal preference. In this application we will use the term "transport bed reactor" to mean any reactor in which solid particles are injected at one end of the reactor and carried along with gas reactants at high velocities and discharged at the other end of the reactor to a gas-solids separation vessel. A riser reactor, in which the reactor is a vertical pipe wherein the reactive solids and gases are fed in at the bottom, transported in essentially plug flow and removed at the top, is one example of a transport bed reactor. Another example is a pipeline reactor, in which the flow of solids and gases is other than vertically upwards. A transport bed reactor, as defined herein, includes a riser reactor or pipeline reactor which also incorporates a zone for fluidization; i.e., a zone where the gas velocities are sufficiently high to carry out a substantial portion of the solids fed, but with more back-mixing of solids than would occur in plug flow. We will use the term "recirculating solids reactor system" to mean a general reaction system with two reaction zones, in which two separate reactions take place, and which uses a particulate solid which circulates between the two reaction zones and takes part in both reactions. Optionally, either or both reaction zones may take place in a transport bed reactor or a fluidized bed. Such reaction systems have found use in catalytic cracking in petroleum refining and in other reactions.

U.S. Pat. No. 4,102,914 discloses a process for the preparation of acrylonitrile by passing a mixture comprising gaseous oxygen, propylene and ammonia, together with an ammoxidation catalyst, in a transport bed reactor while controlling the superficial linear gas velocity and solids feed rate at specific rates.

European Patent Office Publication No. 0 034 442 discloses a process for preparing unsaturated aldehydes by passing an unsaturated olefin and an excess of gaseous oxygen into a transport bed reactor with a solid oxidation catalyst at a linear gas velocity of 1.5 to 7.5 meters/second to achieve substantially plug flow within the reactor. Reaction products are stripped from the catalyst with steam in the stripper chamber.

U.S. Pat. No. 4,668,802 discloses a process for preparing maleic anhydride by oxidizing butane using an oxidized vanadium-phosphorous oxide catalyst as oxidant rather than oxygen wherein the resulting reduced catalyst is separately regenerated, and the use of a recirculating solids reactor system for this reaction. Certain of the examples use a transport bed or riser reactor for the butane oxidation reaction. Japanese Kokai 3-170,445 discloses a similar process for preparing acrolein and acrylic acid by oxidizing propane using an oxidized bismuth-molybdenum catalyst as oxidant.

The concept of using propylene in a similar process to make acrolein was disclosed in a paper titled "Oxidation and Ammoxidation of Propylene over Bismuth Molybdate Catalyst", J. L. Callahan et al, Ind. Eng. Chem. Prod. Res. Develop., Vol. 9, No. 2 (1970). The use of a bismuth molybdate composition as direct oxidant was tested, but under the conditions of their tests this process was judged unsatisfactory because of the large amount of solids requiring circulation. Instead a process of using the bismuth molybdate composition as oxidation catalyst (rather than as direct oxidant) was chosen for commercialization. This paper does not disclose the improved reaction conditions of the present invention.

U.S. Pat. Nos. 4,152,393 and 4,341,717 disclose a specific design of reactor which it is said could be used, among a variety of applications, for the oxidation of propylene to acrolein using an oxidized solids as oxidant and regenerating the resulting reduced solids in its regeneration zone. A process example shows the ammoxidation of propylene using ammonia and an oxidized molybdenum-based catalyst as oxidant. The reactor consists of a single shell containing a reaction zone and a regeneration zone, using a specific design containing a first up-leg, a first down-leg, a second up-leg, a second down-leg and a return leg such that fluidized solids may be transferred from one zone to the other by one route and back by a second route, and so that the gases from one zone are not transferred to the other zone. This reactor has a complicated design which offers numerous places for potential plugging and which limits the ability to independently monitor and control oxidation zone and reduction zone conditions. This patent does not disclose the improved reaction conditions of the present invention.

The concept of using an oxidized catalyst to oxidize propylene was also disclosed in a paper titled "Modeling of Propylene Oxidation in a Circulating Fluidized-bed Reactor", G. S. Patience et al., at a conference named "New Developments in Selective Oxidation II", and published by Elsevier Science B.V. (1994). However, while the theoretical model of this system demonstrated that it had potential use as an alternate reactor system for propylene oxidation, it listed numerous challenges and uncertainties for development of a working process.

U.S. Pat. No. 4,604,370 discloses a process for regenerating a spent molybdenum-bismuth based multi-oxide catalyst resulting from its use for the oxidation of propylene to acrolein by heating it in air to 380 to 500° C. for at least 12 hours or to 500 to 540° C. for at least 2 hours.

An advertising folder prepared by E. I. DuPont in 1973 titled "Chemical Technologies Worldwide" included a single sheet titled "Transport Bed Reactor Technology for Selective Processes", which described the general advantages of a transport bed or riser reactor, listing among typical applications the reaction of propylene to make acrylic acid and the reaction of propylene and ammonia to make acrylonitrile.

None of the above references disclose the necessary information to enable the economical use of a vapor phase process for the oxidation of propylene to acrolein using as oxidant particulate solids in an oxidized state, and where the resulting reduced solids are separately regenerated using molecular oxygen.

The preparation of multicomponent compositions containing molybdenum and/or other metals and their use as catalysts in the oxidation of propylene to make acrolein is well known in the art. For example, U.S. Pat. Nos. 4,677,084 and 4,769,477 disclose a process for making highly attrition resistant silica-based catalysts containing molybdenum, vanadium or other metals. The molybdenum catalyst composition described was stated to show good catalytic performance in a conventional process for making acrylonitrile from propylene and ammonia. Numerous other patents such as U.S. Pat. No. 3,631,099, GB 1,490,489 or JP 05,301,051 also disclose specific catalyst compositions containing molybdenum for use in the oxidation of propylene to acrolein in a fixed-bed or fluidized-bed process.

BRIEF SUMMARY OF THE INVENTION

The present invention relates to a process for the selective vapor oxidation of propylene to acrolein, comprising the steps of: (a) contacting a feed gas containing from 1 mol % to 100 mol % (preferably from 5 mol % to 30 mol %) propylene, 0 to 20 mol % oxygen, 0 to 70 mol % water, and the remainder inert gas with an effective amount of a bismuth molybdate multimetal oxide in oxidized form comprised of particles from 10 to 300 micrometers in size, in a transport bed reactor at a temperature of 250 to 450° C., a gas residence time in the reaction zone from 1 second to 15 seconds, and a solids residence time in the reaction zone from 2 seconds to 60 seconds to convert at least a portion the propylen to acrolein using the bismuth molybdate multimetal oxide solids in oxidized form as a direst oxidant; (b) removing the effluent produced in the transport bed reactor of step (a) and separating the resultant reduced solids from the effluent gases (preferably stripping off any effluent gases from the reduced solids), transporting the reduced solids to a regenerator zone of the recirculating solids reactor system, and recovering acrolein from the effluent gases; (c) oxidizing the reduced bismuth molybdate multimetal oxide in the regenerator zone using an oxygen-containing gas, at a temperature of 250 to 500° C. at a solids residence time in the regenerator zone of 0.5 minute to 10 minutes, and at an oxygen-containing gas residence time from 3 seconds to 30 seconds; and, (d) recycling the oxidized bismuth molybdate multimetal oxide produced in step (c) to the transport bed reactor.

It is an object of this invention to provide an improved vapor phase process using a transport bed reactor for the oxidation of propylene to acrolein using the oxidized form of an attrition resistant solid containing molybdenum, and where the resulting reduced solids are separately regenerated using gaseous oxygen.

DETAILED DESCRIPTION OF INVENTION

Figure 2:
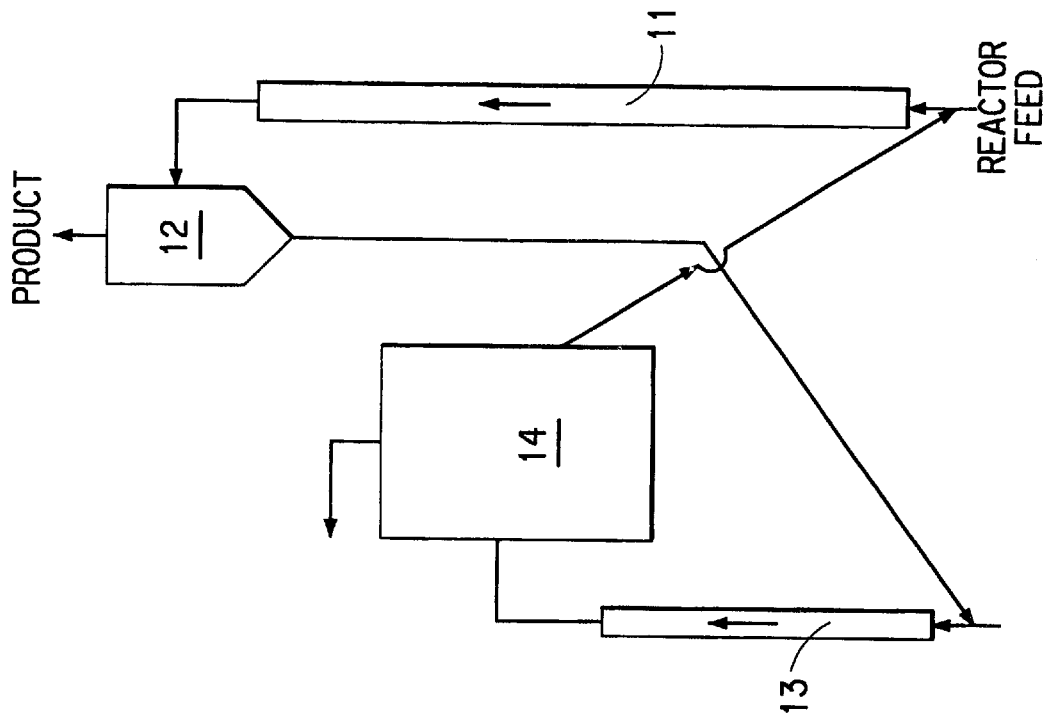
FIG. 2 shows a schematic drawing of a recirculating solids reactor configuration in which the reaction zone is comprised of a riser section and the regeneration zone is comprised of two parts, a riser section and a fluid bed section.

The present invention relates to an improved process for the selective vapor oxidation of propylene to acrolein in a recirculating solids reactor system which includes a transport bed reactor and a solids regenerator. The transport bed reactor is preferably a riser reactor in which solid particles are injected at the bottom of a vertical pipe, carried upwards with gas reactants at high velocities and discharged to a gas-solids separation vessel, or a combination of a riser reactor with a fluidization zone. The reaction between gas and solids occurs in the riser pipe in a matter of seconds, as distinguished from a conventional fluidized bed reactor where the reaction time is a matter of minutes. Gas velocities in a riser reactor are about 2 to 15 times higher than in fluidized bed reactors; solids concentrations range from 2 up to about 40 times lower. The products of the above reaction are then sent to a conventional processing unit where the desired acrolein is separated and recovered with any unreacted gasses being recycled for further processing.

The reduced solids are then re-oxidized in a separate oxidation step to enable their reuse for the oxidation of propylene. The reduced solids from the riser zone are first separated from the product gas, stripped of any carbonaceous species in a separate stripper zone and returned to the regenerator. This process permits independent control of the reactant gas concentrations, the gas residence time, and the solids residence time in each zone for optimum operation.

There are several advantages of the above reactive concept over the steady-state fixed bed or fluidized bed alternative. High selectivity is achieved because of plug flow and optimum oxidative state of the solids. Significant reductions are realized in product recovery costs because the regeneration off-gas stream is kept separate from the product gas stream, resulting in a highly concentrated product stream. High throughput rates are attributed to the independent control of variables for the two steps of the operation, resulting in reduced investment and decreased solids inventory.

When a hydrocarbon oxidation reaction is carried out in the absence of molecular oxygen, lattice oxygen from the surface layers of these mixed metal oxide solids gets consumed very rapidly, typically in a matter of seconds. When that occurs, the solids activity decreases dramatically. If the solid is allowed to remain in the reducing atmosphere, reduced surface layers are built up on an oxidized core because diffusion of the bulk lattice oxygen to the surface is generally very slow in most practical situations. These reduced layers decrease selectivity and cause excessive yield losses when they get oxidized in the solids regenerator to carbon oxides. Previous processes for the oxidation of propylene to acrolein processes which used an oxidant with a separate regeneration zone for the solids do not disclose the surprising benefit of a short residence time in the propylene oxidation/solids reduction zone.

In carrying out the inventive process, the feed gas to the propylene oxidation step contains about 1 mol % to 100 mol % propylene, preferably about 5 mol % to about 30 mol % propylene. Some of the propylene used in the feed may be provided by the unconverted propylene which is present in the recycled reaction gas. In some cases, propylene may be available as the predominant component in a mixture of gases including other hydrocarbons; for example, technical propylene used in industry may contain 95 mol % propylene and 0 to 5 mol % propane. As long as none of the other gases present significantly adversely affects the process, it may be more convenient to use this propylene-rich mixture in the feed gas as the source of propylene. The oxygen concentration in the feed gas can be from 0 to 20 mol %. Air can be used as the source of oxygen. The remainder of the feed can be any inert gas, such as nitrogen or recycled reaction gas containing mostly water, carbon monoxide and carbon dioxide, and possibly unconverted propylene.

The present invention uses an effective amount of a bismuth molybdate multimetal oxide in oxidized form. Preferably this is a specially hardened solid particle which resists attrition, such as disclosed in previously referenced U.S. Pat. Nos. 4,677,084 and 4,769,477. Numerous other bismuth molybdate metal oxide compositions are disclosed in the art for the vapor phase oxidation of propylene to acrolein, and are also suitable for the operation of this invention. It should be further appreciated that other transition metal oxidant systems known in the art to promote the oxidation of propylene to acrolein, such as for example but not by way of limitation the iron/antimony metal oxide solids, should be considered equivalent for purposes of the process of the present invention. The solid particles are preferably about 20 to about 300 micrometers in size.

The oxidation step is carried out in the reaction zone at a temperature of about 250 to about 450° C. The reactor gas exit pressure is typically 0–50 psig. The gas residence time in the reaction zone is about 1 second to about 15 seconds, and the solids residence time in the reaction zone is about 2 seconds to 60 seconds. The upper limit of solids residence time will, of course, depend on the activity of the solids. If still active, the solids can be retained in the reaction zone for longer than 60 seconds. Preferably, the solids are removed from the oxidation step when the oxidative surface layer of the solids have been essentially reduced to a non-oxidized form. The solids in the reactor effluent are separated from the effluent gases, and the acrolein product is recovered from the effluent gases, both separations employing conventional techniques and equipment. The separated solids are referred to herein as the reduced solids because they are in a lower oxidation state than that of the fresh solids which enter the reaction zone. When appropriate to the embodiment, the reduced solids are preferably stripped of any reactor gases and then transported to the regeneration zone of the recirculating solids reactor system. The stripped reactor gases are mixed with the reactor effluent gases. Acrolein is recovered from the effluent gases of the reaction zone, and remaining gases may be vented or recycled to the reaction zone. Any off-gases from the regeneration zone can be vented after heat recovery. Since this reaction is highly exothermic, the heat removal from the recirculating reactor system can be done by use of cooling coils, preferably at the solids regenerator but if necessary also at the fluidization of feed and/or eventually at the riser.

The reduced solids are re-oxidized in the regeneration zone using an oxygen-containing gas such as air. The regeneration zone temperature is maintained at about 250 to about 500° C. The solids residence time in the regenerator zone is about 0.5 minute to, typically, about 10 minutes. The oxygen-containing gas residence time is about 3 seconds to about 30 seconds. Total gas flow rate and oxygen concentration must be sufficient to provide the needed oxygen for solids re-oxidation to occur within the selected gas and solids residence time. The oxidized solids are then recycled to the reaction zone.

The required amount of solids and the required solids circulation rate depend on the extent to which the solids oxidation reaction is carried out in the regeneration zone (as opposed to the reaction zone), the amount of propylene to be reacted, the amount of mobile (or reactive) oxygen contained by the solids, and the reaction zone process conditions that determine the amount of solids oxygen used per pass. When oxygen concentration in the reaction zone is low, or zero, and substantially all of the solids re-oxidation reaction is carried out in the regeneration zone, a high solids circulation rate is required. This rate may be reduced, to the extent that the solids re-oxidation reaction is carried out in the reaction zone.

A recirculating solids reactor system can be operated continuously to oxidize propylene without any gas-phase oxygen in the reaction zone. Such operation results in a higher selectivity to make acrolein than can be attained with conventional reactors, providing an adequate solids circulation rate is maintained to supply the needed oxidized solids. In order to minimize the gas phase oxygen in the reaction zone, gas phase oxygen is stripped from the oxidized solids before recycling them to the reaction zone.

Alternatively, if a recirculating solids reactor system is operated so as to oxidize propylene under conditions of temperature, oxygen and propylene partial pressures and residence time in the reaction zone identical to those used in conventional reactors, significantly higher conversion of propylene and significantly higher yield of acrolein are obtained.

The high selectivity to acrolein attained in the transport bed reactor is maintained even if the feed to the reaction zone has a very high propylene concentration. The gas feed can be 100% propylene.

Recirculating solids reactor systems can in general have many different reactor/regenerator configurations. For example, the reaction zone of the system can be comprised of a transport bed reactor, a fluidized bed reactor or other gas-solid reactors, as can the regeneration zone. The recirculating solids reactor system employed in this invention utilizes a transport bed reactor for the reaction zone. Optionally the transport bed reactor may comprise a riser reactor, a pipeline reactor, or a riser or pipeline reactor combined with a fluidization zone. The regeneration zone of the regenerator can be comprised of a riser reactor, a pipeline reactor, a fluidized bed reactor of any type, or a combination of the above reactors. It is to be understood that the invention is not limited to the specific combination of reactors listed above.

A transport bed reactor is characterized by high gas velocities of from about 5 ft/sec (about 1.5 m/sec) to greater than 40 ft/sec (12 m/sec). At the lower end of the velocity range there can be a significant amount of local back-mixing of solids. Typically, the reactor line is vertically mounted with gas and solids flowing upward in essentially plug flow; i.e., a riser reactor. Preferably, the superficial gas velocity in the riser is maintained at 1 to 10 meters/sec. The flow can also be downward and the reactor line can be mounted other than vertically, i.e., a pipeline reactor.

The solids concentration in the reaction zone of the reactor can range from, typically, about 1 lb/ft$^3$ (16 kg/m$^3$) to, typically, about 10 lb/ft$^3$ (160 kg/m$^3$), depending on the gas velocity, particle size and density, and the solids circulation rate. Preferably, the solids flux (mass flow rate per unit area) is at 50 to 1000 kg/m$^2$. sec.

Figure 1:
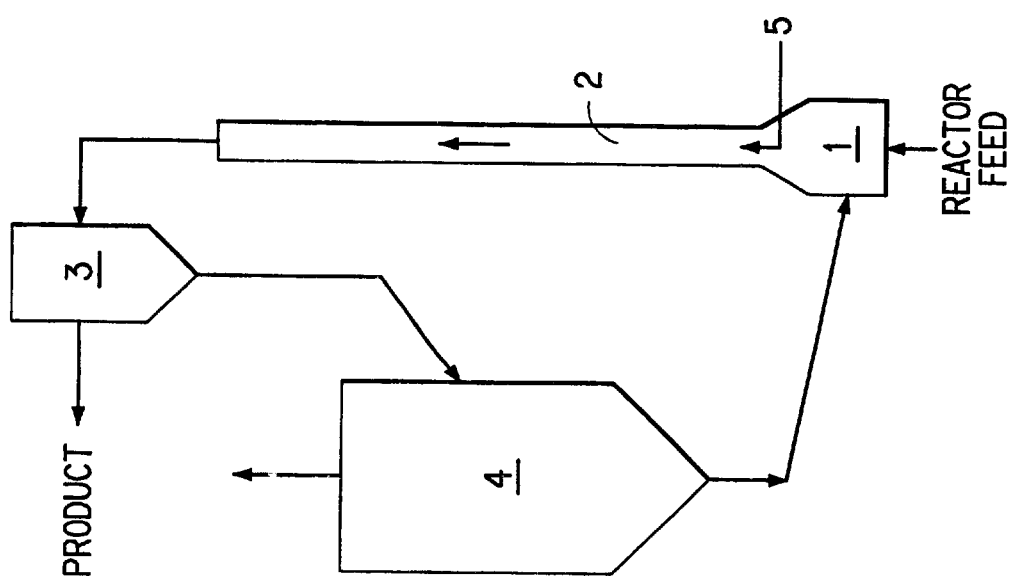
FIG. 1 shows a schematic drawing of a recirculating solids reactor configuration in which the reaction zone is comprised of two parts, a fluid bed section and a riser section and the regeneration zone is comprised of a fluid bed section.

FIG. 1 is a schematic drawing of one of the recirculating solids reactor systems used in the examples. The reaction zone is comprised of a fluidization section 1 and a riser section 2. The feed gas enters 1 and the oxidation of propylene takes place in sections 1 and 2. The separator-stripper unit 3 separates and strips off the reaction zone effluent gases from the reduced solids. The acrolein product is recovered from the reactor effluent gases leaving 3. The reduced solids are transported to the regeneration zone which is comprised of the fluidized bed section 4. The reduced solids are re-oxidized in section 4 and the oxidized (regenerated) solids are then recycled to the fluidization section 1. The alternate/additional feed line 5 can be used to feed additional oxygen to riser section 2. The recirculation solids reactor of this embodiment can also be operated with just the riser section 2 as the reaction zone. In this mode of operation the feed can be introduced into the riser section 2 through feed line 5.

FIG. 2 is a schematic drawing of another recirculating solids reactor system used in the examples. The reaction zone is comprised of a riser section 11. The feed gas enters 11 and the oxidation of propylene takes place in 11. The separator-stripper unit 12 separates and strips off the reaction zone effluent gases from the reduced solids. The acrolein product is recovered from the reactor effluent gases leaving 12. The reduced solids are transported to the regeneration zone which is comprised of a riser section 13 and a fluidized bed section 14. The reduced solids are oxidized in this regeneration zone and the oxidized (regenerated) solids are then recycled to the riser section 11.

The reaction and regeneration zones can be within a single reactor, although better process control usually is achieved if the two are in separate units.

The conversion of propylene in percent is defined as 100 times the number of mols of propylene converted, divided by the number of mols of propylene in the feed. The selectivity to acrolein in percent is defined as 100 times the number of mols of propylene converted to acrolein divided by the total number of mols of propylene converted. The yield of acrolein in percent is defined as 100 times the number of mols of acrolein formed divided by the number of mols of propylene in the feed.

As indicated previously, there are a number of bismuth molybdate oxidants disclosed in the art as suitable for the oxidation of propylene to acrolein. the process of this invention is not limited to a particular method of making this solid, nor to a particular promoter.

The following examples are presented to more fully demonstrate and further illustrate various individual aspects and features of the present invention and the showings are intended to further illustrate the differences and advantages of the present invention. As such the examples are felt to be non-limiting and are meant to illustrate the invention but are not meant to be unduly limiting.

EXAMPLE 1

The attrition resistant solids used in the examples of this invention were prepared by substantially following the procedure in U.S. Pat. No. 4,677,084 and in particular the procedure found in Example 10. The starting solids used to make the attrition resistant solids were obtained following the procedure described in French patent application 97 02343 filed Feb. 27, 1997 in the name of ELF ATOCHEM S.A. and in particular by using multicomponent molybdate obtained according to example 5 of the French patent application. The starting solids prepared according to this French application corresponds to the formula: $Mo_{12}Co_{3.5}Bi_{1.1}Fe_{0.8}W_{0.5}Si_{1.4}K_{0.05}O_x$, where x is the quantity of oxygen bonded to the other elements and depends on their oxidation state. The procedure involved 60.9 grams of $Co(NO_3)_2.6H_2O$ being dissolved in 20 mL of distilled water. Also, 20.2 grams of $Fe(NO_3)_3.9H_2O$ were dissolved in 15 mL of distilled water and 31.2 grams of $Bi(NO_3)_3.5H_2O$ were dissolved in 30 mL of distilled water acidified with 6 mL $HNO_3$ at a concentration of 68% by volume. Separately 127.4 grams of $(NH_4)_6Mo_7O_{24}.4H_2O$ were dissolved in 150 mL of water with heating and stirring then 7.4 grams of $WO_3$ were added. The aqueous solution containing the cobalt was introduced dropwise over 20 minutes into the aqueous solution of the ammonium salts. The ferric solution was next introduced over 10 minutes and then the solution containing the bismuth over 15 minutes. A solution obtained by dissolving 0.2 grams of KOH and 12,8 grams of colloidal silica (at a concentration of 40 weight %) in 15 mL of water was added over 10 minutes to the resulting gel. The gel thus obtained was blended for 1 hour at ambient temperature and then 1 hour at 70° C. The gel was next dried for 18 hours at 130° C. to obtain a solid precursor. The solid obtained was precalcined at about 225° C. in air. This precalcined solid was then milled and mixed with polysilicic acid solution as described in Example 10 of the U.S. Pat. No. 4,677,084. The slurry was then spray dried and the resulting solids were calcined for 9 hours at about 450° C. in air to produce the attrition resistant solids used in the following test 1 through 34 of Example 1.

A recirculating solids reactor system of the type shown in FIG. 1 was used to oxidize propylene to acrolein. The transport bed reactor consisted of a small fluidization section surmounted by a ⅝" diameter by 10' tall riser tube. The recirculating solids were transported up the riser tube with the reactant and product gases which are in plug flow. Reactant gas contact times were on the order of 1–5 seconds. Isothermal conditions were maintained by an electric furnace. Temperatures were maintained in the range of 250–450° C. Reactor pressure was maintained at atmospheric to 2 psig. Riser superficial gas velocity was in the range of 6.6–10.5 ft/sec. Riser gas contact time was in the range of 1.3 to 1.5 seconds. Propylene feed concentration was varied as shown in the tables which follow. Steam feed concentrations were in the range of 9–33 mol %. All feed flows were controlled by thermal mass flow controllers. Propylene and nitrogen were fed either to the fluidization zone or directly to the riser tube (by-passing the fluidization zone).

The solids and the product gas stream were separated in a stripper and a series of cyclones. The stripper was a 4' diameter fluidized bed. After disengagement and stripping from the solids, the product off-gas was fed to the product quench/absorption system. Solids contact time in the stripper was in the range of 15 seconds to 10 minutes. From the stripper, the solids were then transported to the regenerator.

The regenerator was a 4.5" diameter fluidized bed. Solids bed height (solids contact time) in the regenerator was controlled by differential pressure control between the stripper and regenerator. Air was fed to the regenerator to re-oxidize the solids. The solids contact time was in the range of 1–21 minutes. The off-gas from the regenerator off-gas was fed to the regenerator quench system after disengagement from the solids in a series of cyclones.

From the regenerator, the oxidized solids were then fed back to the fluidization section of the transport bed reactor. The solids circulation rate was in the range of 15–250 kg/hr.

The two off-gas quench systems for the product and regenerator off-gases were of identical design. A recirculating liquid served as a direct contact condenser/absorber for the products. Caustic was used on the product off-gas to absorb organic products and to dimerize the acrolein produced. Water was used on the regenerator off-gas.

A hot gas sample stream from the product off-gas was taken to two static water absorbers. The first was used to absorb $C_2/C_3$ aldehydes and acids for quantitative analysis by an off-line gas chromatograph. The second was used as a pre-treatment absorber to remove aldehydes and acids which interfere with the analysis, prior to on-line gas chromatographic analysis of $N_2$, $O_2$, propylene, CO and $CO_2$.

The regenerator off-gas was sampled down-stream of the water quench and analyzed for $N_2$, $O_2$, propylene, CO and $CO_2$. Reactor performance was determined by on-line gas chromatograph analysis for non-absorbed components in each of the two off-gas streams. Water absorbed products were measured by off-line gas chromatograph analysis of the liquid sample absorber.

The composition of the feed gases are presented in the tables as mol % of propylene, steam and nitrogen. If air was employed the amount is identified in a footnote. In some of the tests the contact time may have been increased by directing the gasses to the bottom of the fluidized bed rather than the base of the riser (see FIG. 1 feed line 5). The primary process variables in the tables below are abbreviated as follows: Fluid. Bed Temp ° C. (fluidized bed temperature in ° C.), $C_3H_6$ Feed Conc. mol % (propylene feed concentration in mol percent), Gas Cont. Time sec (gas contact time in seconds),and Sol. Rate kg/hr (solids circulation rate in kilograms per hour). The primary responses were measured as key process variables were changed, and are abbreviated in the tables below as follows: Propylene Conver. % (percent propylene conversion), and $C_3/C_2$ Select. % (percent selectivity to $C_3$ and $C_2$ reaction products).

The tests were grouped into three sets (Tables 1, 2 and 3 below). The first set (Table 1) included tests where all riser side feeds were to the fluidization bed.

TABLE 1

PROCESS VARIABLES

| | Fluid. | $C_3H_6$/steam/$N_2$ | Gas | Sol. | RESPONSES | |
|---|---|---|---|---|---|---|
| Test Num | Bed Temp ° C. | Feed Conc. mol % | Cont Time sec | Circ. Rate kg/hr | Propylene Conver. % | $C_3/C_2$ Select. % |
| 1 | 351 | 10.5/8.8/80.6 | 2.0 | 25 | 22.5 | 85.0 |
| 2 | 352 | 10.5/8.9/80.6 | 2.0 | 23 | 20.2 | 82.2 |
| 3 | 359 | 11.1/9.9/79.0 | 2.3 | 131 | 46.4 | 85.1 |
| 4 | 355 | 11.6/10.0/78.4 | 2.4 | 252 | 61.3 | 83.7 |
| 5 | 351 | 10.6/9.3/80.1 | 2.2 | 30 | 15.5 | 87.7 |
| 6 | 352 | 10.5/9.4/80.1 | 2.1 | 78 | 26.2 | 82.9 |
| 7 | 353 | 10.4/9.3/80.3 | 2.1 | 72 | 30.4 | 83.5 |
| 8 | 350 | 10.6/9.3/80.1 | 2.2 | 72 | 27.2 | 82.5 |
| 9 | 351 | 10.6/9.3/80.1 | 2.3 | 72 | 24.9 | 83.5 |
| 10 | 351 | 10.4/9.1/80.5 | 2.2 | 68 | 37.0 | 87.9 |
| 11 | 352 | 14.7/8.7/76.6 | 2.0 | 58 | 27.1 | 89.3 |
| 12 | 347 | 6.6/9.2/84.2 | 2.2 | 53 | 31.4 | 85.2 |
| 13 | 350 | 9.6/8.4/82.0 | 2.0 | 40 | 26.9 | 88.0 |
| 14 | 350 | 10.5/9.3/80.2 | 2.2 | 135 | 57.0 | 84.3 |
| 15 | 333 | 10.2/8.8/81.0 | 2.2 | 39 | 12.7 | 82.4 |
| 16 | 363 | 10.6/8.7/73.8 | 2.0 | 25 | 48.5 | 86.0 |
| 17 | 373 | 10.6/9.3/80.1 | 2.1 | 23 | 17.9 | 81.4 |

*10 SCFH air feed to fluidization bed (6.8 mol % in feed).

The second set of tests (Table 2) included tests where the nitrogen feed was split between the fluidization bed and the riser to increase gas contact time and propylene concentration in the fluidization bed.

TABLE 2

PROCESS VARIABLES

| | Fluid. | $C_3H_6$/steam/$N_2$ | Gas | Sol. | RESPONSES | |
|---|---|---|---|---|---|---|
| Test Num | Bed Temp ° C. | Feed Conc. mol % | Cont Time sec | Circ. Rate kg/hr | Propylene Conver. % | $C_3/C_2$ Select. % |
| 18 | 352 | 49.4/9.1/41.5 | 3.9 | 17 | 7.9 | 40.3 |
| 19 | 345 | 26.9/9.1/64.0 | 3.1 | 107 | 12.1 | 69.2 |
| 20 | 333 | 33.0/9.2/57.8 | 2.6 | 95 | 23.9 | 89.8 |
| 21 | 328 | 49.1/9.1/41.8 | 3.9 | 13 | 4.5 | 32.5 |
| 22 | 326 | 25.6/9.1/65.3 | 3.0 | 13 | 2.9 | 20.2 |
| 23 | 380 | 26.9/9.3/63.8 | 3.0 | 164 | 43.0 | 67.6 |
| 24 | 383 | 17.0/9.5/73.5 | 2.5 | 30 | 40.4 | 80.6 |
| 25 | 372 | 16.7/9.5/73.8 | 2.5 | 16 | 26.3 | 89.0 |
| 26 | 373 | 10.6/9.3/80.1 | 2.1 | 23 | 17.9 | 81.4 |

The third set of tests (Table 3) included tests where all propylene feed was to the riser (no propylene in the fluidization bed).

TABLE 3

PROCESS VARIABLES

| | Fluid. | $C_3H_6$/steam/$N_2$ | Gas | Sol. | RESPONSES | |
|---|---|---|---|---|---|---|
| Test Num | Bed Temp ° C. | Feed Conc. mol % | Cont. Time sec | Circ. Rate kg/hr | Propylene Conver. % | $C_3/C_2$ Select. % |
| 27 | 350 | 21.1/9.5/69.3 | 1.5 | 18 | 21.3 | 92.3 |
| 28 | 348 | 21.1/9.5/69.3 | 1.5 | 21 | 15.9 | 95.5 |
| 29 | 347 | 24.0/9.6/66.3 | 1.5 | 22 | 15.7 | 94.6 |
| 30 | 347 | 23.8/9.5/66.7 | 1.4 | 19 | 13.1 | 89.2 |
| 31 | 348 | 5.4/9.8/84.8 | 1.5 | 18 | 13.7 | 77.6 |
| 32 | 345 | 21.1/9.5/69.4 | 1.4 | 17 | 17.8 | 91.5 |

TABLE 3-continued

| | | PROCESS VARIABLES | | | RESPONSES | |
|---|---|---|---|---|---|---|
| Test Num | Fluid. Bed Temp ° C. | $C_3H_6$/steam/$N_2$ Feed Conc. mol % | Gas Cont. Time sec | Sol. Circ. Rate kg/hr | Propylene Conver. % | $C_3/C_2$ Select. % |
| 33 | 349 | 10.4/9.4/80.2 | 1.4 | 15 | 17.0 | 84.1 |
| 34* | 349 | 10.2/9.3/73.1 | 1.4 | 18 | 21.0 | 82.1 |

*10 SCFH air feed to fluidized bed (7.4 mol % in feed)

The results were very good with the best results obtained with propylene feed to the riser as in Table 3 (where there is plug flow and no back-mixing of gas). The best test results are as follows:

$C_3/C_2$ Selectivity >95%

Riser+Fluid. Bed Conversion >60%

Solids Conversion Ratio <400 kg/kg

Two tests (shown by *) were run with air feed to the riser. One test was conducted with all feeds to the fluidized bed, and one with propylene feed to the riser. The fluidized bed feed test resulted in significantly higher riser conversion. The riser feed test resulted in somewhat higher conversion and little change to selectivity. The best performances were achieved when fully oxidized solids were reduced in the riser in such a manner that essentially all the readily labile oxygen is consumed and the solids are removed from the reducing atmosphere immediately.

EXAMPLE 2

In a manner similar to the procedure of Example 1, a series of four additional runs were performed in the recirculating solids reactor of the type shown in FIG. 1. In these runs propylene was converted to acrolein using commercially purchased bismuth molybdate multimetal oxide solids as the oxidant. The particular bismuth molybdate multimetal oxide solids employed had a history of being used commercially at DuPont's Beaumont facility for the manufacture of acrylonitrile and been rejuvenated after showing a decline in activity relative to the manufacture of acrylonitrile. The rejuvenation process involved addition of molybdenum to the spent catalyst. Quantitative elemental analysis of several batches of rejuvinated catalyst used in this example established that the empirical formula of the bismuth molybdate multimetal oxide corresponds to the formula; $Ni_{2.1}Co_{3.5}Fe_{2.6}P_{0.43}Bi_{1.0}Mo_{9.3}Mn_{0.15}Cr_{0.09}Ba_{0.07}Zr_{0.0012}K_{0.07}O_x$, where x is the quanitity of oxygen bonded to the other elements and depends on their oxidation state. In addition the analysis indicated that 49.8 wt % $SiO_2$ was present as support. The x-ray diffraction data of the rejuvinated catalyst/oxidant solids can be interpreted as involving a complex phase composition dominated by essentially two phases; namely, $Bi_2Mo_3O_{12}$ and $(Fe_{1/4}Co_{1/2}N_{1/4})MoO_4$. The process variables and test result data are presented in Table 4.

TABLE 4

| | | PROCESS VARIABLES | | | RESPONSES | |
|---|---|---|---|---|---|---|
| Test Num | Fluid. Bed Temp ° C. | $C_3H_6$/steam/$N_2$ Feed Conc. mol % | Gas Cont. Time sec | Sol. Circ. Rate kg/hr | Propylene Conver. % | Acrolein and Acrylic acid Select. % |
| 35 | 346 | 2.0/5.0/93 | 2.4 | 84 | 75.69 | 100 |
| 36 | 346 | 6.0/5.0/89 | 2.4 | 83 | 52.89 | 99.09 |
| 37 | 353 | 10/5.0/85 | 2.4 | 72.7 | 34.33 | 98.45 |
| 38 | 352 | 20/5.0/75 | 2.4 | 61 | 14.55 | 96.25 |

EXAMPLE 3

In a manner analogous to the procedure of Example 1, a series of four additional runs were performed in the recirculating solids reactor of the type shown in FIG. 1. In these runs propylene was converted to acrolein using essentially the same bismuth molybdate multimetal oxide composition as was used in Example 1. The only difference was that the salt precursor after drying was not precalcined at 225° C. in air but instead was directly milled to the desired particle size range and mixed with polysilicic acid solution. This slurry was then spray dried and the resulting solids were precalcined at 225° C. in air and then calcined at 450° C. for 9 hours in air to produce the attrition resistant solids. The process variables and test result data for these additional runs are presented in Table 5.

TABLE 5

| | | PROCESS VARIABLES | | | RESPONSES | |
|---|---|---|---|---|---|---|
| Test Num | Fluid. Bed Temp ° C. | $C_3H_6$/steam/$N_2$ Feed Conc. mol % | Gas Cont. Time sec | Sol. Circ. Rate kg/hr | Propylene Conver. % | Acrolein and Acrylic acid Select. % |
| 39 | 353 | 2.0/5.0/93 | 2.4 | 62 | 67.66 | 93.44 |
| 40 | 348 | 6.0/5.0/89 | 2.4 | 75 | 51.69 | 90.90 |
| 41 | 349 | 10/15.0/85 | 2.4 | 59 | 42.22 | 88.52 |
| 42 | 350 | 20/5.0/75 | 2.4 | 71 | 21.03 | 86.84 |

Having thus described and exemplified the invention with a certain degree of particularity, it should be appreciated that the following claims are not to be so limited but are to be afforded a scope commensurate with the wording of each element of the claim and equivalents thereof.

We claim:

1. A process for the selective vapor phase oxidation of propylene to acrolein, comprising the steps of:

(a) contacting a feed gas containing from 1 mol % to 100 mol % propylene, 0 to 20 mol % oxygen, 0 to 70 mol % water, and the remainder inert gas with an effective amount of the bismuth molybdate multimetal oxide in oxidized form comprised of solid particles from 10 to 300 micrometers in size, in a transport bed reactor at a temperature of 250 to 450° C., a gas residence time in the reaction zone of 1 second to 15 seconds, and a solids residence time in the reaction zone of 2 seconds to 60 seconds to convert at least a portion of said proylene to acrolein using said bismuth molybdate multimetal oxide in oxidized form as a direct oxidant;

(b) removing the effluent produced in the transport bed reactor of step (a) and separating the resultant reduced bismuth molybdate multimetal oxide from the effluent gases, transporting the reduced bismuth molybdate multimetal oxide to a regenerator zone of the recirculating solids reactor system, and recovering acrolein from the effluent gases;

(c) oxidizing the reduced bismuth molybdate multimetal oxide in the regenerator zone using an oxygen containing gas, at a temperature of 250 to 500° C. at a solids residence time in the regenerator zone from 0.5 minute to 10 minutes, and at an oxygen-containing gas residence time from 3 seconds to 30 seconds; and (d) recycling the oxidized bismuth molybdate multimetal oxide produced in step (c) to the transport bed reactor.

2. A process as claimed in claim 1 wherein the feed gas contains from 5 mol % to 30 mol % propylene.

3. A process as claimed in claim 1 wherein the transport bed reactor is a riser or pipeline reactor.

4. A process as claimed in claim 1 where superficial gas velocity in the riser is maintained at 1 to 10 meters/sec.

5. A process as claimed in claim 1 where the bismuth molybdate multimetal oxide flux (mass flow rate per unit area) is at 50 to 1000 kg/sq. meter/sec.

6. A process as claimed in claim 1 where the regenerator zone is a fluidized bed, and the oxygen-containing gas to the regenerator is air.

7. A process as claimed in claim 1 where the bismuth molybdate multimetal oxide was prepared from a multimetal salt slurry by drying the slurry to produce a solid, precalcining the solid at a temperature of about 225° C., milling the precalcined solid to produce particles, adding the solid particles to a polysilicic acid solution, spray drying and calcining the spray dried particles at about 450° C.

8. A process as claimed in claim 1 where the bismuth molybdate multimetal oxide is a commercial grade catalyst that can be used for producing acrylonitrile.

9. A process as claimed in claim 1 where the bismuth molybdate multimetal oxide was prepared from a multimetal salt slurry by drying the slurry to produce a solid, milling this solid to produce particles, adding the solid particles to a polysilicic acid solution, spray drying, precalcining and calcining in air.

10. A process of claim 1 wherein said bismuth molybdate multimetal oxide is $MO_{12}Co_{3.5}Bi_{1.1}Fe_{0.8}WO_{0.5}Si_{1.4}K_{0.05}O_x$, where x is the quanitity of oxygen bonded to the other elements and depends on their oxidation state.

11. A process of claim 1 wherein said bismuth molybdate multimetal oxide is $Ni_{2.1}Co_{3.5}Fe_{2.6}P_{0.43}Bi_{1.0}Mo_{9.3}Mn_{0.15}Cr_{0.09}Ba_{0.07}Zr_{0.0012}K_{0.07}O_x$, where x is the quanitity of oxygen bonded to the other elements and depends on their oxidation state.

* * * * *